United States Patent [19]

Asculai et al.

[11] 4,147,803

[45] Apr. 3, 1979

[54] NONIONIC SURFACE ACTIVE ANTI-VIRAL AGENTS

[75] Inventors: Samuel S. Asculai, Hampton, N.J.; Alfred B. Kupferberg, deceased, late of Somerville, N.J., by Beatrice Kupferberg, coexecutor; by Meyer Halpern, coexecutor, Lauderhill, Fla.

[73] Assignee: Ortho Pharmaceutical Corp., Raritan, N.J.

[21] Appl. No.: 749,957

[22] Filed: Dec. 13, 1976

Related U.S. Application Data

[62] Division of Ser. No. 529,180, Dec. 3, 1974, Pat. No. 4,020,183.

[51] Int. Cl.$^2$ .................. A61K 31/16; A61K 31/335; A61K 31/35; A61K 31/34
[52] U.S. Cl. ................................. 424/320; 424/278; 424/283; 424/285
[58] Field of Search ............... 424/278, 283, 285, 320

[56] References Cited

PUBLICATIONS

Detergents and Emulsifiers, 1963, p. 159.
Detergents and Emulsifiers, 1963, pp. 93 and 105.
Atlas Surfactants and Sorbitol, 1960, p. 49.

*Primary Examiner*—Jerome D. Goldberg
*Attorney, Agent, or Firm*—Benjamin F. Lambert

[57] ABSTRACT

Nonionic surface active anti-viral agents are described. The anti-viral agents are nonionic surfactants and are useful as inactivating agents for herpes simplex.

3 Claims, No Drawings

NONIONIC SURFACE ACTIVE ANTI-VIRAL AGENTS

This is a division, of application Ser. No. 529,180 filed Dec. 3, 1974, now U.S. Pat. No. 4,020,183.

The present invention relates to a method of inactivating herpes simplex virus.

Two types of herpes simplex have been described. The predominant clinical manifestation of type 1 is recurrent herpes labialis (cold sores). Type 2 in man primarily causes recurrent herpetic vulvovaginitis.

Infectivity of herpes simplex viruses is dependent, in part, on the existence of an intact viral envelope. Chemical agents that damage or remove the envelope will dramatically reduce infectivity. Herpes simplex virus envelopes have been shown to be sensitive to lipid solvents, enzymes and detergents. Quaternary ammonium cationic detergents, such as cetyl pyridinium chloride and benzalkonium chloride, are highly effective inactivators of herpes simplex viruses. Certain heterocyclic dyes which affect the viral DNA when exposed to light, while reducing infectivity, also increase the tumor forming potential of herpes simplex viruses. However, no effective prophylactic or therapeutic agent for preventing herpes simplex virus infection exists.

By the present invention a method of inactivating herpes simplex viruses is provided. The viruses are inactivated by treating the infected area with a nonionic surface active agent.

Nonionic surface active agents, in contrast to cationic, anionic and ampholytic surface active agents, contain no ionizable groups and have no surface charge. They depend upon their entire molecule for surface activity. Almost any hydrophobic compound which has in its structure a carboxy, hydroxy, amido or amino group with a free hydrogen attached to the nitrogen, can be reacted with ethylene oxide to form a nonionic surfactant. Nonionic surfactants can be classified in terms of the molecule and at least three groups of nonionic surfactants are recognized:

(1) those having an ether linkage such as the polyoxyethylene alkyl-phenols, polyoxyethylene alcohols, polyoxyethylene esters of fatty acids, polyoxyethylene mercaptans and polyoxyethylene alkyl amines;

(2) those having an ester or ether-ester linkage such as, for example sorbitan monolaurate, sorbitan monopalmitate, sorbitan monostearate, sorbitan tristearate, sorbitan monooleate, sorbitan sesquioleate and sorbitan trioleate; polyoxyethylene (4) sorbitan monolaurate, polyoxyethylene (20) sorbitan monolaurate, polyoxyethylene (20) sorbitan monopalmitate, polyoxyethylene (4) sorbitan monostearate, polyoxyethylene (20) sorbitan tristearate, polyoxyethylene (5) sorbitan monooleate, polyoxyethylene (20) sorbitan monooleate, and polyoxyethylene (20) trioleate; and (3) those having an ether-amide linkage such as, for example, fatty alkanolamides including onyx-ol, unamide, monamine and lauric diethanolamide. Preferred among the nonionic surfactants are p-diisobutylphenoxy-polyethoxyethanol, nonylphenoxypolyethoxyethanol, polyoxyethylene oleyl ether, sorbitan monolaurate, sorbitan monooleate, polysorbate-20, polysorbate-80 and onyx-ol. The ether, amide, ester or ether-ester linkage is between the hydrophobic and hydrophilic portions of the molecule.

DESCRIPTION OF THE PREFERRED EMBODIMENTS

Nonionic agents are becoming a major class of compounds used in pharmaceutical systems. They commonly find use as emulsifiers and, occasionally, as active ingredients. Nonionic surfactants have been employed in topically applied contraceptives due to their spermicidal activity. They have never individually or as a class been reported to affect herpes simplex virus infectivity (HSV).

Herpes simplex virus types 1 and 2 produce a variety of clinical manifestations. In general, herpes simplex virus-1 is associated with a recurrent labialis and herpes simplex virus-2 with recurrent vulvovaginitis.

The ultimate infectivity of HSV resides in the DNA. HSV treated with neutral red, toluidine blue and proflavine (heterocyclic dyes that combine with DNA) have been demonstrated to be susceptible to photodynamic inactivation. Photodynamic inactivation with neutral red has been proposed as a therapeutic regimen in treating recurrent herpetic lesions. Recently, this treatment was challenged by the finding that neutral red-inactivated herpes simplex viruses were capable of transforming cultured mammalian cells. However, infectivity of herpes simplex virus is dependent, in part, on the existence of an intact envelope.

By the present invention it has been demonstrated that nonionic surface active agents having ether or amide or ester linkages either alone or in combination rapidly inactivate herpes simplex virus infectivity. It is believed that they act by damaging or destroying the viral lipid envelope. Support for this mechanism arises from the cytotoxic action of nonionic surfactants against herpes simplex virus. Treatment of RK cells with the surfactant at cytotoxic dilutions, resulted in the destruction of the lipoprotein plasma membrane such that only free nuclei were observed. Since herpes simplex virus envelopes and plasma membranes are believed to be similar in structure and composition, it is conceivable that the destruction of the viral envelope occurs in a fashion analogous to cell membrane destruction. The advantage held by nonionic surfactants in treating herpes simplex virus infectivity lies in the fact that they rapidly inactivate the virus by a mechanism which does not involve the viral genetic material.

For use in treating herpetic lesions, one or more nonionic surfactants is formulated in a pharmaceutically acceptable, non-irrating vehicle. The vehicle may be in any suitable form such as a lotion, cream, oil or emulsion, for example. Suitable pharmaceutically acceptable vehicles include polyethylene glycol, mineral oil, petrolatum, propylene glycol and the like. The formulated nonionic surfactant is then applied topically to the infected area. Treatment is continued until the lesion is healed. The amount of surfactant employed is generally between 0.5% and 20%. The preferred range is 1–5%.

The following are examples of formulations containing a nonionic surfactant:

| Lotion | |
|---|---|
| propylene glycol | 24.75 ml. |
| triethanolamine | 1.00 ml. |
| water | 7.00 ml. |
| oleic acid | 1.50 gm. |
| polyethylene glycol monostearate | 10.50 gm. |
| silicon fluids | 10.00 ml. |
| carbopol-934 (2% mucilage) | 50.00 ml. |

-continued

| Cream | |
|---|---|
| white petrolatum | 41.00 gm. |
| microcrystalline wax | 3.00 gm. |
| fluid lanolin | 10.00 gm. |
| sorbitan monooleate | 4.75 gm. |
| polysorbate-80 | 0.25 gm. |
| purified water | 41.00 gm. |
| spermaceti | 7.5% |
| white wax | 12.0% |
| mineral oil | 56.0% |
| sodium borate | 0.5% |
| sorbitan monooleate | 5.0% |
| purified water | 19.0% |

PREPARATION OF RABBIT KIDNEY CULTURES

Cortical rabbit kidney (RK) cells were prepared by trypsinization from weanling (21-28 day-old) rabbits. The dispersed cells were suspended in Eagle's Basal Medium (BME) containing Earl's Salts and supplemented with 10% fetal bovine serum (FBS), 10% tryptose phosphate broth, and 100 units penicillin, 100 ug. streptomycin per ml. Monolayer cultures were established in plastic, 75 cm² tissue culture (T-75) flasks for preparation of virus stocks, and plastic, 60×15 mm. Petri dishes for virus assay. Cultures were grown in a humidified atmosphere of 5% $CO_2$ in air at 35°.

VIRUS GROWTH

Confluent monolayers of RK cells grown in T-75 flasks were infected with approximately $10^6$ plaque forming units (PFU) of HSV. Viruses were harvested, when 75% of the cells exhibited cytopathology, by scraping the monolayer with a rubber policeman, freezing and thawing the cells twice in an ethanol-dry ice bath, and sedimenting the debris by centrifugation at 2,000 RPM for five minutes. Virus stocks were kept frozen, in one ml. aliquots at −70°.

VIRUS TITRATIONS

Confluent monolayers of RK cells in 60 mm. plastic Petri dishes were used for determining the number PFU per unit volume of virus stock. Serial 10-fold dilutions of virus were made in tris (hydroxymethyl) aminomethane (TRIS) buffer pH 7.4; 0.5 ml. aliquots of each dilution are added to duplicate RK cultures. HSV-1 and HSV-2 were allowed to adsorb at room temperature with frequent rocking to insure uniform distribution of the inoculum. After 1.5 hours, unadsorbed virus is removed and the infected cells overlayered with 5 ml. of 0.5% methyl cellulose (4000 cps.) in BME supplemented with 10% FBS. After a four-day incubation at 35° C., the overlay is removed and the cell sheet exposed to 0.1% ethanolic crystal violet for 1-2 minutes. HSV plaques are visible as clear areas in a blue background after the dye is removed and the plates air-dried.

INACTIVATION OF HSV BY NONIONIC SURFACTANTS

One ml. of virus stock is mixed with either one ml. of surfactant, appropriately diluted in TRIS buffer. The mixture is immediately immersed into a 37° C. water bath and held for one minute. Confluent monolayers of RK cells in 60 mm. plastic Petri dishes are used for determining the number of PFU per unit volume of treated virus stock. Serial 10-fold dilutions of the mixture are made in tris (hydroxymethyl) aminomethane (TRIS) buffer pH 7.4; 0.5 ml. aliquots of each dilution are added to duplicate RK cultures. HSV-1 and HSV-2 are allowed to adsorb at room temperature with frequent rocking to insure uniform distribution of the inoculum. After 1.5 hours, unadsorbed virus is removed and the infected cells overlayered with 5 ml. of 0.5% methyl cellulose (4000 cps.) in BME supplemented with 10% FBS. After a four-day incubation at 35° C., the overlay is removed and the cell sheet exposed to 0.1% ethanolic crystal violet for 1-2 minutes. The absence of or the reduction in the number of plaques is an indication of the inactivation of the virus.

The effect of several nonionic surfactants on herpes simplex virus is illustrated in Table 1. The results indicate that nonionic surface active agents are active in reducing HSV infectivity. A 1.0 hour exposure of RK cells to dilutions of less than 1:500 of the surfactant solution resulted in cell destruction. This effect correlates with the anti-viral activity of the agent, i.e., surfactants which inactivate HSV are cytotoxic at dilutions less than 1:500.

TABLE 1

| INACTIVATION OF HERPES SIMPLEX VIRUSES BY NON-IONIC SURFACE ACTIVE AGENTS | | | |
|---|---|---|---|
| Hydrophilic-Hydrophobic Linkage | Surfactant | HSV-1 Virus Titer PFU/ml. | HSV-2 Virus Titer PFU/ml. |
| Ether | Nonylphenoxypolyethoxy ethanol (5%) | <500 | <500 |
| Ether | p-Diisobutyl-phenoxy-Polyethoxyethanol (1%) | <500 | <500 |
| Ether | Polyoxyethylene (10) oleyl Ether (1%) | <500 | <500 |
| Ester | Sorbitan Monolaurate (1%) | $8.8 \times 10^6$ | $6.1 \times 10^5$ |
| Ester | Sorbitan Monooleate (1%) | $8.0 \times 10^6$ | $5.1 \times 10^5$ |
| Ether-Ester | Polysorbate 20 (1%) | $4.3 \times 10^6$ | $5.4 \times 10^5$ |
| Ether-Ester | Polysorbate 80 (1%) | $9.2 \times 10^6$ | $6.5 \times 10^5$ |
| Amide | Onyx-ol 345 (1%) | <500 | <500 |
| Control Virus | | $1.9 \times 10^7$ | $1 \times 10^6$ |

What is claimed is:

1. A method of inactivating herpes simplex virus infectivity in humans which comprises applying to the affected area an effective amount for treating herpes simplex virus of lauric diethanolamide in a pharmaceutically acceptable carrier.

2. The method of claim 1 wherein the amount of surfactant present is between 0.5 and 20%.

3. The method of claim 1 wherein the carrier is selected from the group consisting of polyethylene glycol, mineral oil, petrolatum and propylene glycol.

* * * * *